US005723007A

United States Patent [19]
Engel et al.

[11] Patent Number: 5,723,007
[45] Date of Patent: Mar. 3, 1998

[54] BIOCOMPATIBLE COMPOSITE MATERIAL AND PROCESS FOR ITS PRODUCTION

[75] Inventors: Eva Maria Engel; Hugo Haemmerle, both of Tuebingen; Guenter Hoff, Daisendorf; Otto Inacker, Reutlingen; Bernhard Kneissel, Marl; Wilfried Nisch, Tuebingen; Lutz Scheideler, Tuebingen; Heiner Weber, Tuebingen, all of Germany

[73] Assignee: Huels Aktiengesellschaft, Marl, Germany

[21] Appl. No.: 694,020

[22] Filed: Aug. 8, 1996

[30] Foreign Application Priority Data

Aug. 8, 1995 [DE] Germany .................. 195 29 036.4

[51] Int. Cl.$^6$ ................................................ A61F 2/02
[52] U.S. Cl. ............................................................ 623/11
[58] Field of Search ................................. 623/11, 16, 18, 623/20, 21, 1

[56] References Cited

U.S. PATENT DOCUMENTS 5,002,583   3/1991   Pitaru et al. ........................ 623/66
5,320,886   6/1994   Bowen ............................... 428/34.1

*Primary Examiner*—John G. Weiss
*Assistant Examiner*—John M. Black
*Attorney, Agent, or Firm*—Oblon, Spivak, McClelland, Maier & Neustadt, P.C.

[57] ABSTRACT

A biocompatible composite material and a method for its production are provided, wherein the composite material is made of a plastic matrix having a felt of collagen fibers contained therein, wherein the collagen fibers project out of a surface of the composite material, wherein the composite material is produced by a process involving:

a) providing a collagen fiber felt wherein the collagen fibers have a structure of native collagen;

b) impregnating the collagen fiber felt with one or more polymerizable monomers, c) partially curing the one or more polymerizable monomers to provide a polymer containing unpolymerized monomers, shortchain oligomers or both therein;

d) removing the unpolymerized monomers and shortchain oligomers from the surface of the composite material to expose the collagen fiber felt on the surface, wherein the composite material is useful for the production of implants, especially dental implants and the implants can be colonized with human cells prior to implantation.

18 Claims, No Drawings

BIOCOMPATIBLE COMPOSITE MATERIAL AND PROCESS FOR ITS PRODUCTION

BACKGROUND OF THE INVENTION

1. Field of the Invention

The present invention relates to a biocompatible composite material for the production of hard implants a process for its production.

2. Discussion of the Background

Implants to replace organs, vessels or limbs whose function is impaired in the human body are of increasing importance in medicine. A distinction is made between soft implants, such as artificial blood vessels, and hard implants, such as artificial hip joints and dental implants.

The use of collagen to produce a hard implant material corresponds to the state of the art because the substance of bone contains collagen. A number of published patent applications describe the use of collagen for the production of hard implants:

DE-A 25 02 884 describes a liquid or plastic, collagen-containing polymer which produces a union between the actual implant and bone and which cures after application in situ, in the human body.

DE-A 34 14 924 describes the anchoring part of an implant, consisting of a spherical material that is obtained by bonding particles of solid calcium compounds with collagen or another binder.

EP-A-0 202 917 describes the production of plastic implants onto which fibrous materials such as collagen are bonded with the aid of a silicone adhesive.

DE-A 36 27 316 describes collagen fibers that project out of the matrix of an implant material that does not contain colonized human cells.

However, each of these known implant materials are lacking in the level of biocompatibility desired in implants.

DE-A 40 40 872 discloses the colonization of dental implants with human cells. However, these dental implants do not use a specific, cell-compatible implant material. The use of collagen is also mentioned in DE 40 40 872. This collagen is intended to have an adhesive function for the human cells and is applied to the surface of the implant.

SUMMARY OF THE INVENTION

Accordingly, one object of the present invention is to provide a composite material that provides the requisite level of biocompatibility needed for use in implants.

Another object of the present invention is to provide a process for the production of such a composite material.

Another object of the present invention is to provide an implant prepared from the composite material of the present invention.

These and other objects of the present invention have been satisfied by the discovery of a biocompatible composite material comprising a plastic matrix having a felt of collagen fibers contained therein, wherein the collagen fibers project out of a surface of the composite material, wherein the composite material is produced by a process comprising:

a) providing a collagen fiber felt wherein the collagen fibers have a structure of native collagen;

b) impregnating the collagen fiber felt with one or more polymerizable monomers, c) partially curing the one or more polymerizable monomers to provide a polymer containing unpolymerized monomers, shortchain oligomers or both therein;

d) removing the unpolymerized monomers and shortchain oligomers from a surface of the composite material to expose said collagen fiber felt on said surface.

DETAILED DESCRIPTION OF THE PREFERRED EMBODIMENTS

The present invention relates to a composite material for the production of hard implants which comprises, in a specific arrangement, fine-fiber collagen, wherein the implants made therefrom are colonized with human cells before implantation. The composite material is constructed of a network of fine collagen fibers in a plastic, with exposure of free collagen fibers on the material surface, which form a collagen felt and are anchored in the composite material. The surface collagen fiber felt, along with the human cells colonized in the composite implantation, confers a high degree of biocompatibility on implants produced from this material.

The present invention accordingly relates to a biocompatible composite material comprising a felt of collagen fibers and a plastic contained therein, with collagen fibers projecting out of the surface, obtained by a) producing a suitable collagen base with formation of a fiber felt of collagen having the structure of natural collagen, b) impregnating the collagen fiber felt with one or more polymerizable monomers, c) curing a portion of the monomers by exposure to light and/or heat in an oxygen-containing environment, to provide a polymer d) removing any unpolymerized monomers or short-chain oligomers from the surface of the composite material to expose the ends of the collagen fibers forming the felt.

The present invention further relates to an implant produced from the present biocompatible composite material.

The present invention uses collagen which is present in the very fine-fiber, native structure. Further, the present invention provides a collagen-containing composite material with collagen fibers that are exposed on the surface and form a felt. The present invention also colonizes the implants with human cells before the implants are implanted.

Use of a fine-fiber collagen

The high biocompatibility of the implant material of the present invention results from the fine collagen fibers on the implant surface, which are anchored in the implant material. These fibers have a diameter of about 200 nanometers and correspond in their structure to native collagen. For this reason, the collagen fibers formed by human cells unite with the collagen fibers of the composite material and ensure favorable incorporation of the implants.

The usual commercially obtainable collagen products are more or less denatured, with loss of their native structure.

The following process can be used to produce the fine-fiber collagen with the native structure required in the present invention: collagen, such as that from bovine or rat tail tendons, is dissolved in dilute acetic acid (preferably 0.1 to 5.0% strength, more preferably from 0.1 to 1.0% strength, most preferably 0.5% strength) and subsequently purified by dialysis and centrifugation. The centrifuge supernatant containing the collagen molecules is then removed and transferred into sterile vessels. Alteration of the pH (preferably to a pH of from 2–7, more preferably 3–5, most preferably pH=4) and of the salt concentration results in the collagen molecules becoming organized in felt-like mats of fine-fiber collagen.

Production of the Composite Material

Crucial for successful application of a collagen-containing composite material is exposure of the native collagen fibers on the surface during production.

This is achieved with the present composite material by impregnating the collagen mats with curable monomers, such as methyl methacrylate monomer (MMA), subsequently curing with light or heat and then removing the topmost layer of the collagen/PMMA composite material for partial exposure of the collagen fibers (exposed felt).

A process based on the principle of inhibition of the MMA polymerization reaction on the surface by atmospheric oxygen is preferably used for this. In this process, the collagen mats are impregnated with the MMA monomer mixture are polymerized, not in closed molds, but with access for atmospheric oxygen. Since the MMA polymerization reaction is inhibited by atmospheric oxygen, an uncured outer layer remains on the surface of the samples and is subsequently removed, such as by treatment with a solvent, such as acetone. It is possible to expose the collagen fibers on the surface in this way. The thickness of the layer can be controlled by the choice of the appropriate parameters (oxygen concentration, duration of the curing process, light intensity, temperature).

It is possible in principle to use as curable monomers any monomer that polymerizes by free-radical reaction polymerization, such as styrene, alkyl acrylates and methacrylates, where the alkyl group can contain 1 to 12C atoms. The monomer structure can be linear, branched, cycloaliphatic, aromatic or substituted aromatic. It is also possible to use heterocyclic monomers which have either nitrogen, sulfur or oxygen in the side chain. The monomers can be used as single components or in the form of monomer mixtures or monomer/polymer mixtures with or without fillers.

Examples of suitable preferred monofunctional monomers include:
methyl methacrylate,
ethyl methacrylate,
n-butyl methacrylate,
isobutyl methacrylate,
2-ethylhexyl methacrylate,
cyclohexyl methacrylate,
isobornyl methacrylate,
tetrahydrofurfuryl methacrylate,
benzyl methacrylate, and
morpholinoethyl methacrylate Examples of suitable preferred crosslinking monomers include:
diethylene glycol dimethacrylate, triethylene glycol dimethacrylate, diurethane dimethacrylate (product of the reaction of trimethylhexamethylene diisocyanate with two mol of 2-hydroxyethyl methacrylate), and isopropylidenebis (2(3)-hydroxy-3(2)-(4-phenoxy)propyl methacrylate) ("bis-GMA")

Colonization of the Implant Surface with Human Cells

The cells with which the implant surface according to this invention is colonized are fibroblasts, cells that produce connective tissue fibers (=collagen fibers). The implant material according to the present invention contains, on its surface, collagen fibers in their native structure. The present implant material is thus a particularly suitable substrate for colonization by these fibroblasts and affords, in the form of the fine-fiber collagen network, good opportunities for anchoring of the collagen fibers formed by the fibroblasts.

The intimate union produced with this anchoring, between the implant collagen fibers and the collagen fibers that are synthesized de novo by the fibroblasts and have a connective tissue function, leads to rapid biological incorporation of the implants of the composite material according to the present invention.

Having generally described this invention, a further understanding can be obtained by reference to certain specific examples which are provided herein for purposes of illustration only and are not intended to be limiting unless otherwise specified.

EXAMPLES:

Example 1

Production of Fine-Fiber Mats from Native Rat Tail Collagen

Comminuted and defibrated tendons from 10 to 14 rat tails were washed in double-distilled water and then incubated in 800 ml of 0.5% strength acetic acid with stirring at 4° C. for 3 days, during which the collagen fibers disintegrated into soluble collagen molecules. The solution of collagen subunits obtained in this way was filtered through absorbent gauze and dialyzed against a total of 10 liters of cell culture medium (Dulbecco's minimal essential medium, DMEM), which was diluted 1:10, at pH=4 and at 4° C. for two days.

Centrifugation of a dialyzate produced in this way at 25,000 g for 24 hours resulted in a clear supernatant of dissolved collagen, which was stored in sterile vessels at 4° C. The collagen molecules in this solution organized themselves in the medium which is described below to form a gel of fine collagen fibers with the structure of nature collagen.

Adjustment of the Gelling Medium

Solutions required:

Solution A: Fetal calf serum

Solution B: 1.7 ml of 10-fold concentrated PBS (without $Ca^{2+}$ and $Mg^{2+}$); 0.3 ml of 1M HEPES; 0.15 ml of 10% $NaHCO$.

Solution C: 0.142N NaOH

Solution D: Collagen solution, pH=4

A polymerization solution was first produced from 165 μl of A, 110 μl of B and 40 μl of C. 315 μl of polymerization solution were mixed with 685 μl of collagen solution D. A collagen gel which consisted of a fine-fiber collagen mat as supporting structure was formed after about 10 sec.

The gels were incubated at 37° C. in 95% rel. humidity for 30 min for definitive curing and subsequently transferred into an increasing alcohol series described below.

Removal of water in increasing alcohol series:

| Ethanol concentration | Time |
| --- | --- |
| 30% | 15 min. |
| 50% | 15 min. |
| 70% | 60 min. |
| 95% | 10 min. |
| 99% | 20 min. |
| 100% | 20 min. |
| 100% | 20 min. |
| 100% | 20 min. |

After transfer into alcohol, the mats were either impregnated directly from the liquid phase with monomer mixture or else subjected in acetone to a critical point drying in liquid $CO_2$.

The process described above resulted in two different collagen base materials for producing composite materials:

1. mats of native collagen in alcohol, for direct impregnation with MMA 2. mats of native collagen, critical point-dried, for placing on MMA, thus impregnating the mats.

Example 2

Production of a composite material, embodiment A: (completely impregnated materials)

Composite materials were produced using a lightcuring methacrylate monomer mixture supplied by Kulzer. The product is available under the name DURAFILL FLOW and is used in dentistry as a filling material. Filler particles are added to DURAFILL FLOW in the commercial form.

1 g of paste contained:

| | |
|---|---|
| Isopropylidenebis[2(3')-hydroxy-3(2)-(4-phenoxy)-propyl methacrylate] | 62 mg |
| (2,2(4),4-Trimethylhexa-methylenebis(2-carbamoyl-oxyethyl)] dimethacrylate | 153 mg |
| 3,6-Dioxaoctamethylenedimethacrylate | 132 mg |
| Silicon dioxide silanized with (3-methacryloyloxy-propyl)trimethoxysilane | 304 mg |
| Polymer chips[silicon dioxide/poly(dodeca-methylene dimethacrylate)] | 328 mg |

To produce the composite materials described herein, Kulzer manufactured a Durafill monomer mixture without fillers.

Collagen mats floating in alcohol (see Example 1) were used as starting material to produce completely impregnated composite materials. The mats were impregnated with Durafill monomer mixture in several steps as follows:

| | | |
|---|---|---|
| 1. Ethanol/MMA 1:1 | 0.5 h | |
| 2. Ethanol/MMA 1:1 | 1.5 h | |
| 3. Pure MMA solution | 12.0 h | |
| 4. Pure MMA solution | 6.0 h | |

In the impregnation, the samples were moved slowly on an inclined rotator.

The filtered samples were placed on filter paper in order to allow excess MMA to drain off, and subsequently cured under a halogen lamp (Delolux 03E, Delo) for 10 min. The samples were then etched in an acetone bath with continuous agitation for 10 min. in order to remove the unpolymerized layer on the surface. The bath liquid was changed three times during this process.

Example 3

Production of a composite material, variant B: (composite material that contains collagen only on the surface)

These materials were produced using native, critical point-dried collagen mats 3–5 mm thick.

Glass molds were made in order to allow light to reach the sample from all sides during the photopolymerization. The molds were filled with monomer mixture, and the dried collagen mats were placed on top and allowed to sink for about 15 sec. The polymerization subsequently took place under a halogen lamp, for 5 min. each from above and below. After removal of the excess collagen residues on the surface, the samples were etched in acetone and, at the same time, cleaned with ultrasound.

Example 4

Production of an implant consisting of a biocompatible layer on a metallic support Collagen mats with a volume of 25 ml were produced as described in Example 1 and impregnated with MMA monomer mixture. The impregnated mats were subsequently partially disintegrated in a mixer. This process led to a viscous mixture of MMA and collagen fibers. The mixture was applied in a layer thickness of about 1 mm to cylindrical implants made of pure titanium (length 18 mm, $\phi$ 3.5 mm) and cured by light-curing on a rotating apparatus for 5 minutes.

The collagen fibers on the surface were subsequently exposed by acetone etching.

Example 5

The biocompatibility of the collagen/PMMA materials mentioned in Example 2 and 3 was tested in cell culture tests. This entailed investigation of 1) the speed of colonization of the surface of these materials with cells, 2) the adhesion and spread of the cells and 3) the synthesis and adhesion of a connective tissue matrix of collagen fibers due to these cells on the surface of the materials. This took place by direct comparison of the materials with an endogenous hard material (tooth root surface) in a conventional test model known from dental research (root disk culture model (see A. B. Bernstein et al. (1988) Cell Tissue Res. 254: 659–70).

Test Procedure:

Human desmodontal cells (desmodontal fibroblasts) were cultivated at a cell density of $1 \times 10^4$ cells/cm$^2$ in Petri dishes in an atmosphere of 5% $O_2$ and 13% $CO_2$ at 37° C. and 98% humidity for 7 days in Dulbecco's minimal essential medium (DMEM). During this time, the cells formed a continuous cell lawn on the base of the Petri dish. The samples were arranged in opposite pairs, with a space of about 100 µm between the pairs of samples, on these cell lawns.

The samples were produced as follows.

1. Material samples: blocks of collagen/PMMA composite materials were cut, using a diamond wire saw, into disks 300 µm thick, subsequently cleaned by ultrasonic treatment and sterilized for use in the cell culture.

2. Tooth disks (reference): tooth root disks from human tooth material were obtained from freshly extracted human wisdom teeth. For this purpose, the tooth root was initially cleaned on the surface by scraping off the desmodontal material using a scalpel and subsequently cut into disks 300 µm thick. The disks were subsequently sterilized and used pairwise in the cell culture.

Results:

The collagen/PMMA composite material surfaces were rapidly and completely colonized by the cells. After 3 weeks in the cell culture, the cells had produced the first collagen fibers between the two opposite sample surfaces. The collagen matrix became consolidated during culturing over four months to a dense network of connective tissue collagen fibers.

After 50 and 100 days, pull tests were carried out to test the adhesion of the newly formed connective tissue fiber union. For this purpose, the material samples, which were in each case located in opposite pairs and between which the cells had formed a dense collagen matrix during the culture, were pulled apart in a tensile testing machine.

The pull resistances for the human tooth disks used as control were measured at 0.2 N/mm$^2$. The materials obtained by impregnation of collagen mats with MMA monomer (Example 2) achieved about 0.15N/mm$^2$. Resistances of 0.16 N/mm$^2$ were achieved with the composite materials produced by the lay-on technique (Example 3).

The results of these tests show that a durable, adhesive attachment of connective tissue collagen fibers to the surface is achieved with the composite materials produced in this way. These composite materials therefore afford excellent conditions for both rapid and permanent incorporation in the body.

This application is based on German Patent Application 195 29 036.4, filed with the German Patent Office on Aug. 8, 1995, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A biocompatible composite material comprising a plastic matrix having a felt of collagen fibers contained therein, wherein said collagen fibers project out of a surface of said composite material, wherein the composite material is produced by a process comprising:
   a) providing a collagen fiber felt wherein said collagen fibers have a structure of native collagen;
   b) impregnating the collagen fiber felt with one or more polymerizable monomers,
   c) partially curing the one or more polymerizable monomers to provide a polymer containing unpolymerized monomers, shortchain oligomers or both therein;
   d) removing the unpolymerized monomers and shortchain oligomers from the surface of said composite material to expose said collagen fiber felt on said surface.

2. The biocompatible composite material as claimed in claim 1, wherein said one or more polymerizable monomers are selected from the group consisting of acrylates and methacrylates.

3. The biocompatible composite material as claimed in claim 2, wherein said one or more polymerizable monomers are methacrylates.

4. The biocompatible composite material as claimed in claim 2, wherein said one or more polymerizable monomers are selected from the group consisting of methyl methacrylate, ethyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diethylene glycol dimethacrylate, triethylene glycol dimethacrylate, diurethane dimethacrylate formed by reaction of trimethylhexamethylene diisocyanate with two mol of 2-hydroxyethyl methacrylate, isopropylidenebis-(2 (3)-hydroxy-3(2)-(4-phenoxy)propyl methacrylate), and mixtures thereof.

5. The biocompatible composite material as claimed in claim 1, wherein said step c) is performed by application of heat or light.

6. The biocompatible composite material as claimed in claim 1, wherein said step d) is performed by treating said surface with acetone to remove said unpolymerized monomers and said shortchain oligomers.

7. The biocompatible composite material as claimed in claim 1, wherein said one or more polymerizable monomers is methyl methacrylate.

8. A process for the production of a biocompatible composite material comprising a plastic matrix having a collagen fiber felt contained therein, wherein said collagen fiber felt projects out of a surface of the composite material, said process comprising:
   a) providing a collagen fiber felt wherein said collagen fibers have a structure of native collagen;
   b) impregnating the collagen fiber felt with one or more polymerizable monomers,
   c) partially curing the one or more polymerizable monomers to provide a polymer containing unpolymerized monomers, shortchain oligomers or both therein;
   d) removing the unpolymerized monomers and shortchain oligomers from a surface of said composite material to expose said collagen fiber felt on said surface.

9. The process as claimed in claim 8, wherein said one or more polymerizable monomers are selected from the group consisting of acrylates and methacrylates.

10. The process as claimed in claim 9, wherein said one or more polymerizable monomers are methacrylates.

11. The process as claimed in claim 9, wherein said one or more polymerizable monomers are selected from the group consisting of methyl methacrylate, ethyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diethylene glycol dimethacrylate, triethylene glycol dimethacrylate, diurethane dimethacrylate formed by reaction of trimethylhexamethylene diisocyanate with two mol of 2-hydroxyethyl methacrylate, isopropylidenebis-(2(3)-hydroxy-3(2)-(4-phenoxy)propyl methacrylate), and mixtures thereof.

12. The process as claimed in claim 8, wherein said step c) is performed by application of heat or light.

13. The process as claimed in claim 8, wherein said step d) is performed by treating said surface with acetone to remove said unpolymerized monomers and said shortchain oligomers.

14. The process as claimed in claim 8, wherein said one or more polymerizable monomers is methyl methacrylate.

15. An implant produced from a biocompatible composite material as claimed in claim 1.

16. The implant as claimed in claim 15, wherein said surface having an exposed collagen fiber felt has human cells thereon.

17. The implant as claimed in claim 15, wherein said implant is colonized by human cells before implantation.

18. The implant as claimed in claim 15, wherein the implant is at least partly or completely a dental prosthesis.

* * * * *